United States Patent
Cohen et al.

(10) Patent No.: US 12,402,596 B2
(45) Date of Patent: Sep. 2, 2025

(54) MILK CHANNEL AND FEED INLET COUPLED THERETO, AND SYSTEM AND METHOD FOR CONSERVING WASH FLUID IN A WASHING PROCESS FOR CLEANING A MILKMETER SYSTEM

(71) Applicant: S.C.R. (Engineers) Limited, Netanya (IL)

(72) Inventors: Mordehay Cohen, Netanya (IL); Yoni Kaminsky, Netanya (IL); Yosef Artzi, Netanya (IL); Taras Khomitsky, Netanya (IL); Eden Weinberg, Netanya (IL); Alexander Gershikov, Netanya (IL)

(73) Assignee: S.C.R. (Engineers) Limited, Netanya (IL)

( * ) Notice: Subject to any disclaimer, the term of this patent is extended or adjusted under 35 U.S.C. 154(b) by 577 days.

(21) Appl. No.: 17/735,123

(22) Filed: May 3, 2022

(65) Prior Publication Data
US 2023/0354766 A1 Nov. 9, 2023

(51) Int. Cl.
*A01J 7/02* (2006.01)
*A01J 5/01* (2006.01)
*B08B 9/032* (2006.01)
*G01F 1/661* (2022.01)
*G01N 33/04* (2006.01)

(52) U.S. Cl.
CPC . *A01J 7/02* (2013.01); *A01J 5/01* (2013.01); *B08B 9/0325* (2013.01); *G01F 1/661* (2013.01); *G01N 33/04* (2013.01)

(58) Field of Classification Search
CPC .... A01J 7/02; A01J 5/01; G01N 33/04; G01F 1/661; B08B 9/0325
See application file for complete search history.

(56) References Cited

U.S. PATENT DOCUMENTS

| | | | |
|---|---|---|---|
| 85,575 A | 1/1869 | Drake | |
| 1,016,752 A | 2/1912 | Leith | |
| 1,139,589 A * | 5/1915 | Sinclair | A01J 5/04 119/14.35 |
| 1,188,510 A | 6/1916 | Timson | |
| 1,364,137 A | 1/1921 | Pannier | |

(Continued)

FOREIGN PATENT DOCUMENTS

| AU | 199534570 | 10/1994 |
|---|---|---|
| AU | 2003239832 | 5/2002 |

(Continued)

OTHER PUBLICATIONS

Christian Pahl, Eberhard Hartung, Anne Grothmann, Katrin Mahlkow-Nerge, Angelika Haeussermann, Rumination activity of dairy cows in the 24 hours before and after calving, Journal of Dairy Science, vol. 97, Issue 11, 2014, pp. 6935-6941.

(Continued)

*Primary Examiner* — Benjamin L Osterhout
(74) *Attorney, Agent, or Firm* — S.J. Intellectual Property LTD.

(57) ABSTRACT

A device comprising a milk channel is disclosed. The milk channel has a first part and a second part, wherein a first value of at least one optical property of the first part is different than a second value of the optical property of the second part.

5 Claims, 5 Drawing Sheets

(56) References Cited

U.S. PATENT DOCUMENTS

| | | | |
|---|---|---|---|
| 1,405,166 A * | 1/1922 | Shippert | A01J 5/04 |
| | | | 119/14.44 |
| 1,759,400 A | 5/1930 | Hobbs | |
| 1,843,314 A | 2/1932 | Berntson et al. | |
| 1,863,037 A | 6/1932 | Archbold | |
| 2,078,827 A | 4/1937 | Ketchum | |
| 2,420,020 A | 5/1947 | Snell | |
| 2,553,400 A | 5/1951 | Blair | |
| 2,570,048 A | 10/1951 | Cooke et al. | |
| 2,626,590 A * | 1/1953 | Smith | A01J 5/041 |
| | | | 251/287 |
| 2,731,300 A * | 1/1956 | Jansen | A01J 7/04 |
| | | | 239/536 |
| 3,091,770 A | 6/1963 | McMurray et al. | |
| 3,261,243 A | 7/1966 | Ellison | |
| 3,596,541 A | 8/1971 | Bieganski | |
| 3,812,859 A | 5/1974 | Murphy et al. | |
| 3,884,100 A | 5/1975 | Fideldy | |
| 3,981,209 A | 9/1976 | Caroff | |
| 4,120,303 A | 10/1978 | Villa-Massone et al. | |
| 4,121,591 A | 10/1978 | Hayes | |
| 4,281,657 A | 8/1981 | Ritchey | |
| 4,323,183 A | 4/1982 | Duchin | |
| 4,344,385 A * | 8/1982 | Swanson | A01J 7/005 |
| | | | 119/14.08 |
| 4,497,321 A | 2/1985 | Fearing et al. | |
| 4,516,577 A | 5/1985 | Scott et al. | |
| 4,531,520 A | 7/1985 | Reggers et al. | |
| 4,552,147 A | 11/1985 | Gardner | |
| 4,666,436 A | 5/1987 | McDonald et al. | |
| 4,672,966 A | 6/1987 | Haas, Jr. | |
| 4,696,119 A | 9/1987 | Howe et al. | |
| 4,716,899 A | 1/1988 | Haas et al. | |
| 4,819,639 A | 4/1989 | Gardner | |
| 4,821,683 A | 4/1989 | Veldman | |
| 4,943,294 A | 7/1990 | Knapp | |
| 5,022,253 A | 6/1991 | Parlatore | |
| 5,056,385 A | 10/1991 | Petersen | |
| 5,080,041 A * | 1/1992 | Steingraber | A01J 7/005 |
| | | | 119/14.55 |
| 5,116,119 A | 5/1992 | Brayer | |
| 5,141,514 A | 8/1992 | van Amelsfort | |
| 5,154,721 A | 10/1992 | Perez | |
| 5,245,946 A | 9/1993 | Hoefelmayr | |
| 5,267,464 A | 12/1993 | Cleland | |
| 5,509,291 A | 4/1996 | Nilsson et al. | |
| 5,581,086 A | 12/1996 | Ben-Menachem | |
| D377,588 S | 1/1997 | Birkholz | |
| 5,651,791 A | 7/1997 | Zavlodaver et al. | |
| 5,778,820 A | 7/1998 | van der Lely et al. | |
| 5,996,529 A * | 12/1999 | Sissom | A01J 5/01 |
| | | | 119/14.14 |
| 6,007,548 A | 12/1999 | Ritchey | |
| 6,016,769 A | 1/2000 | Forster | |
| 6,043,748 A | 3/2000 | Touchton et al. | |
| 6,053,926 A | 4/2000 | Luehrs | |
| 6,095,915 A | 8/2000 | Battista et al. | |
| 6,099,482 A | 8/2000 | Brune et al. | |
| 6,100,804 A | 8/2000 | Brady et al. | |
| 6,113,539 A | 9/2000 | Ridenour | |
| 6,114,957 A | 9/2000 | Westrick et al. | |
| 6,145,225 A | 11/2000 | Ritchey | |
| 6,166,643 A | 12/2000 | Janning et al. | |
| 6,172,640 B1 | 1/2001 | Durst et al. | |
| 6,197,538 B1 | 3/2001 | Van den Berg | |
| 6,232,880 B1 | 5/2001 | Anderson et al. | |
| 6,235,036 B1 | 5/2001 | Gardner et al. | |
| 6,271,757 B1 | 8/2001 | Touchton et al. | |
| 6,297,045 B1 | 10/2001 | Takahashi | |
| 6,297,505 B1 | 10/2001 | Frandsen | |
| 6,297,739 B1 | 10/2001 | Small | |
| 6,310,553 B1 | 10/2001 | Dance | |
| 6,402,692 B1 | 6/2002 | Morford | |
| 6,497,197 B1 | 12/2002 | Huisma | |
| 6,502,060 B1 | 12/2002 | Christian | |
| 6,510,630 B1 | 1/2003 | Gardner | |
| 6,535,131 B1 | 3/2003 | Bar-Shalom et al. | |
| 6,543,382 B1 * | 4/2003 | Kolstad | A01J 5/041 |
| | | | 119/14.54 |
| 6,569,092 B1 | 5/2003 | Booker | |
| 6,659,039 B1 | 12/2003 | Larsen | |
| 6,722,208 B2 | 4/2004 | Brown et al. | |
| 6,731,100 B1 | 5/2004 | Hansen | |
| 6,868,804 B1 | 3/2005 | Huisma et al. | |
| 7,016,730 B2 | 3/2006 | Ternes | |
| 7,046,152 B1 | 5/2006 | Peinetti et al. | |
| 7,137,359 B1 | 11/2006 | Braden | |
| 7,236,237 B2 | 6/2007 | Schmilovitch | |
| 7,296,539 B2 | 11/2007 | Iljas | |
| 7,380,518 B2 | 6/2008 | Kates | |
| D584,121 S | 1/2009 | Fancelli | |
| 7,681,523 B2 | 3/2010 | Holmertz | |
| 7,705,736 B1 | 4/2010 | Kedziora | |
| 7,843,350 B2 | 11/2010 | Geissler et al. | |
| 7,937,861 B1 | 5/2011 | Zacher | |
| 8,005,624 B1 | 8/2011 | Starr | |
| 8,266,990 B1 | 9/2012 | Janson | |
| 8,305,220 B2 | 11/2012 | Gibson | |
| 8,478,389 B1 | 7/2013 | Brockway et al. | |
| 8,622,929 B2 | 1/2014 | Wilson et al. | |
| 8,763,557 B2 | 7/2014 | Lipscomb et al. | |
| 8,955,462 B1 | 2/2015 | Golden et al. | |
| 9,215,862 B2 | 12/2015 | Bladen et al. | |
| 9,392,767 B2 | 7/2016 | Johnson, III et al. | |
| 9,392,946 B1 | 7/2016 | Sarantos et al. | |
| 9,449,487 B1 | 9/2016 | Spitalny | |
| 9,506,856 B2 | 11/2016 | Krief | |
| 9,648,849 B1 | 5/2017 | Vivathana | |
| 9,654,925 B1 | 5/2017 | Solinsky et al. | |
| 9,693,536 B1 | 7/2017 | Dana | |
| 9,717,216 B1 | 8/2017 | Schlachta et al. | |
| 9,743,643 B1 | 8/2017 | Kaplan et al. | |
| 9,848,577 B1 | 12/2017 | Brandao et al. | |
| 9,861,080 B1 | 1/2018 | Hathway et al. | |
| 9,927,273 B2 | 3/2018 | Brown | |
| D818,783 S | 5/2018 | Wermeille | |
| D823,079 S | 7/2018 | Lyytikainen | |
| 10,021,857 B2 | 7/2018 | Bailey et al. | |
| 10,039,263 B2 | 8/2018 | Teychene et al. | |
| 10,045,511 B1 | 8/2018 | Yarden et al. | |
| 10,064,391 B1 | 9/2018 | Riley | |
| 10,091,972 B1 | 10/2018 | Jensen et al. | |
| 10,231,442 B1 | 3/2019 | Chang et al. | |
| 10,242,547 B1 | 3/2019 | Struhsaker et al. | |
| 10,264,762 B1 | 4/2019 | Lamb | |
| 10,352,759 B1 | 7/2019 | Jensen | |
| 10,446,006 B1 | 10/2019 | Johnson, Jr. et al. | |
| 10,512,430 B1 | 12/2019 | Hladio | |
| 10,588,295 B1 | 3/2020 | Riley | |
| 10,628,756 B1 | 4/2020 | Kuper et al. | |
| 10,638,726 B1 | 5/2020 | Makarychev et al. | |
| 10,691,674 B2 | 6/2020 | Leong et al. | |
| 11,644,453 B2 | 5/2023 | Alatorre Llaguno | |
| 2001/0027751 A1 | 10/2001 | van den Berg | |
| 2002/0010390 A1 | 1/2002 | Guice et al. | |
| 2002/0021219 A1 | 2/2002 | Edwards | |
| 2002/0091326 A1 | 7/2002 | Hashimoto et al. | |
| 2002/0095828 A1 | 7/2002 | Koopman et al. | |
| 2002/0154015 A1 | 10/2002 | Hixson | |
| 2002/0158765 A1 | 10/2002 | Pape et al. | |
| 2003/0004925 A1 | 1/2003 | Brunner et al. | |
| 2003/0023517 A1 | 1/2003 | Marsh et al. | |
| 2003/0062001 A1 | 4/2003 | Hakan | |
| 2003/0066491 A1 | 4/2003 | Stampe | |
| 2003/0144926 A1 | 7/2003 | Bodin et al. | |
| 2003/0146284 A1 | 8/2003 | Schmit et al. | |
| 2003/0149526 A1 | 8/2003 | Zhou et al. | |
| 2003/0177025 A1 | 9/2003 | Curkendall et al. | |
| 2003/0201931 A1 | 10/2003 | Durst et al. | |
| 2003/0208157 A1 | 11/2003 | Eidson et al. | |
| 2003/0221343 A1 | 12/2003 | Volk et al. | |
| 2003/0229452 A1 | 12/2003 | Lewis | |
| 2004/0066298 A1 | 4/2004 | Schmitt et al. | |

(56) References Cited

U.S. PATENT DOCUMENTS

| | | |
|---|---|---|
| 2004/0078390 A1 | 4/2004 | Saunders |
| 2004/0118920 A1 | 6/2004 | He |
| 2004/0123810 A1 | 7/2004 | Lorton et al. |
| 2004/0177011 A1 | 9/2004 | Ramsay et al. |
| 2004/0201454 A1 | 10/2004 | Waterhouse et al. |
| 2005/0010333 A1 | 1/2005 | Lorton et al. |
| 2005/0026181 A1 | 2/2005 | Davis et al. |
| 2005/0097997 A1 | 5/2005 | Hile |
| 2005/0108912 A1 | 5/2005 | Bekker |
| 2005/0115508 A1 | 6/2005 | Little |
| 2005/0128086 A1 | 6/2005 | Brown et al. |
| 2005/0139168 A1 | 6/2005 | Light et al. |
| 2005/0145187 A1 | 7/2005 | Gray |
| 2005/0273117 A1 | 12/2005 | Teychene |
| 2005/0279287 A1 | 12/2005 | Kroeker |
| 2005/0284381 A1 | 12/2005 | Bell et al. |
| 2006/0011145 A1 | 1/2006 | Kates |
| 2006/0052986 A1 | 3/2006 | Rogers et al. |
| 2006/0064325 A1 | 3/2006 | Matsumoto et al. |
| 2006/0087440 A1 | 4/2006 | Klein |
| 2006/0106289 A1 | 5/2006 | Elser |
| 2006/0117619 A1 | 6/2006 | Costantini |
| 2006/0155172 A1 | 7/2006 | Rugg |
| 2006/0170561 A1 | 8/2006 | Eyal |
| 2006/0173367 A1 | 8/2006 | Stuart et al. |
| 2006/0185605 A1 | 8/2006 | Renz et al. |
| 2006/0201436 A1 | 9/2006 | Kates |
| 2006/0207515 A1 | 9/2006 | Palett |
| 2006/0241521 A1 | 10/2006 | Cohen |
| 2006/0282274 A1 | 12/2006 | Bennett |
| 2006/0290514 A1 | 12/2006 | Sakama et al. |
| 2007/0006494 A1 | 1/2007 | Hayes et al. |
| 2007/0008155 A1 | 1/2007 | Trost et al. |
| 2007/0021660 A1 | 1/2007 | Delonzor et al. |
| 2007/0027375 A1 | 2/2007 | Melker et al. |
| 2007/0027377 A1 | 2/2007 | Delonzor et al. |
| 2007/0027379 A1 | 2/2007 | Delonzor et al. |
| 2007/0028953 A1 | 2/2007 | Zanot |
| 2007/0029381 A1 | 2/2007 | Braiman |
| 2007/0044317 A1 | 3/2007 | Critelli |
| 2007/0044732 A1 | 3/2007 | Araki et al. |
| 2007/0062457 A1 | 3/2007 | Bates et al. |
| 2007/0069899 A1 | 3/2007 | Shih et al. |
| 2007/0103296 A1 | 5/2007 | Paessel et al. |
| 2007/0149871 A1 | 6/2007 | Sarussi et al. |
| 2007/0152825 A1 | 7/2007 | August et al. |
| 2007/0222624 A1 | 9/2007 | Eicken et al. |
| 2007/0255124 A1 | 11/2007 | Pologe et al. |
| 2007/0258625 A1 | 11/2007 | Mirtsching |
| 2007/0283791 A1 | 12/2007 | Engvall et al. |
| 2007/0298421 A1 | 12/2007 | Jiang et al. |
| 2008/0001815 A1 | 1/2008 | Wang et al. |
| 2008/0004798 A1 | 1/2008 | Troxler et al. |
| 2008/0017126 A1 | 1/2008 | Adams et al. |
| 2008/0018481 A1 | 1/2008 | Zehavi |
| 2008/0021352 A1 | 1/2008 | Keegan et al. |
| 2008/0036610 A1 | 2/2008 | Hokuf et al. |
| 2008/0047177 A1 | 2/2008 | Hilpert |
| 2008/0055155 A1 | 3/2008 | Hensley et al. |
| 2008/0059263 A1 | 3/2008 | Stroman et al. |
| 2008/0061990 A1 | 3/2008 | Milnes et al. |
| 2008/0076988 A1 | 3/2008 | Sarussi et al. |
| 2008/0076992 A1 | 3/2008 | Hete et al. |
| 2008/0085522 A1 | 4/2008 | Meghen et al. |
| 2008/0097726 A1 | 4/2008 | Lorton et al. |
| 2008/0110406 A1 | 5/2008 | Anderson et al. |
| 2008/0146890 A1 | 6/2008 | LeBoeuf et al. |
| 2008/0173255 A1 | 7/2008 | Mainini et al. |
| 2008/0190202 A1 | 8/2008 | Kulach et al. |
| 2008/0190379 A1 | 8/2008 | Mainini et al. |
| 2008/0215484 A1 | 9/2008 | Oldham |
| 2008/0227662 A1 | 9/2008 | Stromberg et al. |
| 2008/0228105 A1 | 9/2008 | Howell et al. |
| 2008/0262326 A1 | 10/2008 | Hete et al. |
| 2008/0272908 A1 | 11/2008 | Boyd |
| 2008/0312511 A1 | 12/2008 | Osler et al. |
| 2009/0009388 A1 | 1/2009 | Wangrud |
| 2009/0020613 A1 | 1/2009 | Chang et al. |
| 2009/0025651 A1 | 1/2009 | Lalor |
| 2009/0058730 A1 | 3/2009 | Geissler et al. |
| 2009/0094869 A1 | 4/2009 | Geissler et al. |
| 2009/0102668 A1 | 4/2009 | Thompson et al. |
| 2009/0139462 A1 | 6/2009 | So |
| 2009/0149727 A1 | 6/2009 | Truitt et al. |
| 2009/0187392 A1 | 7/2009 | Riskey et al. |
| 2009/0255484 A1 | 10/2009 | Muelken |
| 2009/0312667 A1 | 12/2009 | Utsunomiya et al. |
| 2010/0018363 A1 | 1/2010 | Chervenak et al. |
| 2010/0030036 A1 | 2/2010 | Mottram et al. |
| 2010/0045468 A1 | 2/2010 | Geissler |
| 2010/0113902 A1 | 5/2010 | Hete et al. |
| 2010/0139575 A1 | 6/2010 | Duncan et al. |
| 2010/0160809 A1 | 6/2010 | Laurence et al. |
| 2010/0175625 A1 | 7/2010 | Klenotiz |
| 2010/0217102 A1 | 8/2010 | LeBoeuf et al. |
| 2010/0250198 A1 | 9/2010 | Lorton et al. |
| 2010/0275849 A1* | 11/2010 | Wulle ..................... A01J 5/08 119/14.47 |
| 2010/0289639 A1 | 11/2010 | Gibson et al. |
| 2010/0315241 A1 | 12/2010 | Jow |
| 2010/0321182 A1 | 12/2010 | Wangrud |
| 2010/0321189 A1 | 12/2010 | Gibson et al. |
| 2010/0331739 A1 | 12/2010 | Afikim et al. |
| 2011/0018717 A1 | 1/2011 | Takahashi et al. |
| 2011/0061605 A1 | 3/2011 | Hardi et al. |
| 2011/0095089 A1 | 4/2011 | Kolton et al. |
| 2011/0121356 A1 | 5/2011 | Krawinkel et al. |
| 2011/0137185 A1 | 6/2011 | Hete et al. |
| 2011/0152876 A1 | 6/2011 | Vandeputte |
| 2011/0178423 A1 | 7/2011 | Hatch |
| 2011/0203144 A1 | 8/2011 | Junek et al. |
| 2011/0258130 A1 | 10/2011 | Grabiner et al. |
| 2011/0272470 A1 | 11/2011 | Baba et al. |
| 2011/0313264 A1 | 12/2011 | Hete |
| 2012/0009943 A1 | 1/2012 | Greenberg et al. |
| 2012/0068848 A1 | 3/2012 | Campbell et al. |
| 2012/0089152 A1 | 4/2012 | Lynd et al. |
| 2012/0092132 A1 | 4/2012 | Holme et al. |
| 2012/0111286 A1 | 5/2012 | Lee et al. |
| 2012/0112917 A1 | 5/2012 | Menachem et al. |
| 2012/0160181 A1 | 6/2012 | So et al. |
| 2012/0175412 A1 | 7/2012 | Grabiner et al. |
| 2012/0204811 A1 | 8/2012 | Ryan |
| 2012/0236690 A1 | 9/2012 | Rader et al. |
| 2012/0291715 A1 | 11/2012 | Jiang et al. |
| 2012/0299731 A1 | 11/2012 | Triener |
| 2012/0326862 A1 | 12/2012 | Kwak et al. |
| 2012/0326874 A1 | 12/2012 | Kwak et al. |
| 2013/0006065 A1 | 1/2013 | Yanai et al. |
| 2013/0014706 A1 | 1/2013 | Menkes |
| 2013/0046170 A1 | 2/2013 | Haynes |
| 2013/0113622 A1 | 5/2013 | Pratt et al. |
| 2013/0119142 A1 | 5/2013 | McCoy et al. |
| 2013/0175347 A1 | 7/2013 | Decaluwe et al. |
| 2013/0192526 A1 | 8/2013 | Mainini |
| 2013/0211773 A1 | 8/2013 | Loeschinger et al. |
| 2013/0222141 A1 | 8/2013 | Rhee et al. |
| 2013/0237778 A1 | 9/2013 | Rouquette et al. |
| 2013/0239904 A1 | 9/2013 | Kim et al. |
| 2013/0239907 A1 | 9/2013 | Laurence et al. |
| 2013/0265165 A1 | 10/2013 | So et al. |
| 2013/0285815 A1 | 10/2013 | Jones, II |
| 2014/0073486 A1 | 3/2014 | Ahmed et al. |
| 2014/0122488 A1 | 5/2014 | Jung et al. |
| 2014/0123912 A1 | 5/2014 | Menkes et al. |
| 2014/0135596 A1 | 5/2014 | LeBoeuf et al. |
| 2014/0135631 A1 | 5/2014 | Brumback et al. |
| 2014/0171762 A1 | 6/2014 | LeBoeuf et al. |
| 2014/0174376 A1 | 6/2014 | Touchton et al. |
| 2014/0196673 A1 | 7/2014 | Menkes et al. |
| 2014/0230755 A1 | 8/2014 | Trenkle et al. |
| 2014/0232541 A1 | 8/2014 | Trenkle et al. |
| 2014/0253709 A1 | 9/2014 | Bresch et al. |
| 2014/0261235 A1 | 9/2014 | Rich et al. |

(56) References Cited

U.S. PATENT DOCUMENTS

| | | |
|---|---|---|
| 2014/0267299 A1 | 9/2014 | Couse |
| 2014/0275824 A1 | 9/2014 | Couse |
| 2014/0276089 A1 | 9/2014 | Kirenko et al. |
| 2014/0290013 A1 | 10/2014 | Eidelman et al. |
| 2014/0302783 A1 | 10/2014 | Aiuto et al. |
| 2014/0331942 A1 | 11/2014 | Sarazyn |
| 2014/0333439 A1 | 11/2014 | Works |
| 2014/0347184 A1 | 11/2014 | Triener |
| 2014/0352632 A1 | 12/2014 | McLaughlin |
| 2014/0368338 A1 | 12/2014 | Rettedal et al. |
| 2015/0025394 A1 | 1/2015 | Hong et al. |
| 2015/0039239 A1 | 2/2015 | Shuler et al. |
| 2015/0057963 A1 | 2/2015 | Zakharov et al. |
| 2015/0097668 A1 | 4/2015 | Toth |
| 2015/0099472 A1 | 4/2015 | Ickovic |
| 2015/0100245 A1 | 4/2015 | Huang et al. |
| 2015/0107519 A1 | 4/2015 | Rajkondawar et al. |
| 2015/0107522 A1 | 4/2015 | Lamb |
| 2015/0122893 A1 | 5/2015 | Warther |
| 2015/0128873 A1 | 5/2015 | Prescott et al. |
| 2015/0130617 A1 | 5/2015 | Triener |
| 2015/0148811 A1 | 5/2015 | Swope et al. |
| 2015/0157435 A1 | 6/2015 | Chasins et al. |
| 2015/0182322 A1 | 7/2015 | Couse et al. |
| 2015/0245592 A1 | 9/2015 | Sibbald et al. |
| 2015/0282457 A1 | 10/2015 | Yarden |
| 2015/0334994 A1 | 11/2015 | Prasad |
| 2015/0342143 A1 | 12/2015 | Stewart |
| 2015/0351885 A1 | 12/2015 | Kool et al. |
| 2015/0366166 A1 | 12/2015 | Mueller |
| 2016/0000045 A1 | 1/2016 | Funaya et al. |
| 2016/0021506 A1 | 1/2016 | Bonge, Jr. |
| 2016/0058379 A1 | 3/2016 | Menkes et al. |
| 2016/0066546 A1 | 3/2016 | Borchersen et al. |
| 2016/0100802 A1 | 4/2016 | Newman |
| 2016/0106064 A1 | 4/2016 | Bladen et al. |
| 2016/0113524 A1 | 4/2016 | Gross et al. |
| 2016/0120154 A1 | 5/2016 | Hill et al. |
| 2016/0128637 A1 | 5/2016 | LeBoeuf et al. |
| 2016/0135431 A1 | 5/2016 | Siegel |
| 2016/0148086 A1 | 5/2016 | Clarke et al. |
| 2016/0150362 A1 | 5/2016 | Shaprio et al. |
| 2016/0151013 A1 | 6/2016 | Atallah et al. |
| 2016/0165851 A1 | 6/2016 | Harty et al. |
| 2016/0165852 A1 | 6/2016 | Goldfain |
| 2016/0166761 A1 | 6/2016 | Piehl et al. |
| 2016/0198957 A1 | 7/2016 | Arditi et al. |
| 2016/0210841 A1 | 7/2016 | Huang et al. |
| 2016/0213317 A1 | 7/2016 | Richardson et al. |
| 2016/0278712 A1 | 9/2016 | Sagara et al. |
| 2016/0286757 A1 | 10/2016 | Armstrong |
| 2016/0287108 A1 | 10/2016 | Wei et al. |
| 2016/0317049 A1 | 11/2016 | LeBoeuf et al. |
| 2016/0345881 A1 | 12/2016 | Sarantos et al. |
| 2016/0360733 A1 | 12/2016 | Triener |
| 2016/0367495 A1 | 12/2016 | Miller et al. |
| 2017/0000090 A1 | 1/2017 | Hall |
| 2017/0006836 A1 | 1/2017 | Torres |
| 2017/0042119 A1 | 2/2017 | Garrity |
| 2017/0067770 A1 | 3/2017 | Sun |
| 2017/0079247 A1 | 3/2017 | Womble et al. |
| 2017/0095206 A1 | 4/2017 | Leib et al. |
| 2017/0156288 A1 | 6/2017 | Singh |
| 2017/0164905 A1 | 6/2017 | Gumiero |
| 2017/0193208 A1 | 7/2017 | Ashley et al. |
| 2017/0196203 A1 | 7/2017 | Huisma et al. |
| 2017/0202185 A1 | 7/2017 | Trumbull et al. |
| 2017/0245797 A1 | 8/2017 | Quinn |
| 2017/0258039 A1 | 9/2017 | Lauterbach |
| 2017/0272842 A1 | 9/2017 | Touma |
| 2017/0280675 A1 | 10/2017 | Macneil et al. |
| 2017/0280688 A1 | 10/2017 | Deliou et al. |
| 2017/0318781 A1 | 11/2017 | Rollins et al. |
| 2017/0360004 A1 | 12/2017 | Carver |
| 2017/0372583 A1 | 12/2017 | Lamkin et al. |
| 2018/0000045 A1 | 1/2018 | Bianchi et al. |
| 2018/0007863 A1 | 1/2018 | Bailey et al. |
| 2018/0014512 A1 | 1/2018 | Arabani et al. |
| 2018/0055016 A1 | 3/2018 | Hsieh et al. |
| 2018/0064068 A1 | 3/2018 | McKee et al. |
| 2018/0070559 A1 | 3/2018 | So |
| 2018/0098522 A1 | 4/2018 | Steinfort |
| 2018/0110205 A1 | 4/2018 | Czarnecky et al. |
| 2018/0131074 A1 | 5/2018 | Wilkinson et al. |
| 2018/0132455 A1 | 5/2018 | Pradeep et al. |
| 2018/0206455 A1 | 7/2018 | Thiex et al. |
| 2018/0242860 A1 | 8/2018 | LeBoeuf et al. |
| 2018/0249683 A1 | 9/2018 | Borchersen et al. |
| 2018/0260976 A1 | 9/2018 | Watanabe et al. |
| 2018/0271058 A1 | 9/2018 | Valdez |
| 2018/0279582 A1 | 10/2018 | Yajima et al. |
| 2018/0288968 A1 | 10/2018 | Cisco et al. |
| 2018/0295809 A1 | 10/2018 | Yajima et al. |
| 2018/0303425 A1 | 10/2018 | Wordham et al. |
| 2018/0310526 A1 | 11/2018 | Birch et al. |
| 2018/0325382 A1 | 11/2018 | Brandao et al. |
| 2018/0332989 A1 | 11/2018 | Chiu et al. |
| 2018/0333244 A1 | 11/2018 | Hanks et al. |
| 2019/0008118 A1 | 1/2019 | Keegan |
| 2019/0008124 A1 | 1/2019 | Komatsu et al. |
| 2019/0029226 A1 | 1/2019 | Triener |
| 2019/0053469 A1 | 2/2019 | Mardirossian |
| 2019/0053470 A1 | 2/2019 | Singh et al. |
| 2019/0059335 A1 | 2/2019 | Crider, Jr. et al. |
| 2019/0059337 A1 | 2/2019 | Robbins |
| 2019/0059741 A1 | 2/2019 | Crider, Jr. et al. |
| 2019/0069512 A1 | 3/2019 | Eriksson et al. |
| 2019/0075945 A1 | 3/2019 | Strassburger et al. |
| 2019/0082654 A1 | 3/2019 | Robbins |
| 2019/0090754 A1 | 3/2019 | Brandao et al. |
| 2019/0110433 A1 | 4/2019 | Myers |
| 2019/0110436 A1 | 4/2019 | Gardner et al. |
| 2019/0125509 A1 | 5/2019 | Hotchkin |
| 2019/0130728 A1 | 5/2019 | Struhsaker |
| 2019/0133086 A1 | 5/2019 | Katz et al. |
| 2019/0159428 A1 | 5/2019 | Bolen |
| 2019/0166802 A1 | 6/2019 | Seltzer et al. |
| 2019/0183091 A1 | 6/2019 | Betts-LaCroix et al. |
| 2019/0183092 A1 | 6/2019 | Couse et al. |
| 2019/0208358 A1 | 7/2019 | de Barros et al. |
| 2019/0213860 A1 | 7/2019 | Shaprio et al. |
| 2019/0254599 A1 | 8/2019 | Young et al. |
| 2019/0287429 A1 | 9/2019 | Dawson et al. |
| 2019/0290133 A1 | 9/2019 | Crider et al. |
| 2019/0290847 A1 | 9/2019 | Veyrent et al. |
| 2019/0298226 A1 | 10/2019 | Filipowicz |
| 2019/0298924 A1 | 10/2019 | Gibson et al. |
| 2019/0327939 A1 | 10/2019 | Sharpe et al. |
| 2019/0335715 A1 | 11/2019 | Hicks et al. |
| 2019/0350168 A1 | 11/2019 | Shi |
| 2019/0365324 A1 | 12/2019 | Chang |
| 2019/0373857 A1 | 12/2019 | Leigh-Lancaster et al. |
| 2019/0380311 A1 | 12/2019 | Crouthamel et al. |
| 2019/0385037 A1 | 12/2019 | Robadey et al. |
| 2019/0385332 A1 | 12/2019 | Yajima et al. |
| 2020/0015740 A1 | 1/2020 | Alnofeli et al. |
| 2020/0037886 A1 | 2/2020 | Greer et al. |
| 2020/0068853 A1 | 3/2020 | Radovcic |
| 2020/0085019 A1 | 3/2020 | Gilbert et al. |
| 2020/0100463 A1 | 4/2020 | Rooda et al. |
| 2020/0107522 A1 | 4/2020 | Kersey et al. |
| 2020/0110946 A1 | 4/2020 | Kline et al. |
| 2020/0113728 A1 | 4/2020 | Spector et al. |
| 2020/0170222 A1 | 6/2020 | Gotts |
| 2020/0178505 A1 | 6/2020 | Womble et al. |
| 2020/0178800 A1 | 6/2020 | Geissler et al. |
| 2020/0205381 A1 | 7/2020 | Wernimont et al. |
| 2020/0229391 A1 | 7/2020 | De Groot |
| 2020/0229707 A1 | 7/2020 | Donnelly |
| 2020/0242551 A1 | 7/2020 | Lau et al. |

(56) References Cited

U.S. PATENT DOCUMENTS

| | | | |
|---|---|---|---|
| 2021/0262869 | A1 | 8/2021 | Pinsky et al. |
| 2023/0129837 | A1 | 4/2023 | Orchard |

FOREIGN PATENT DOCUMENTS

| | | |
|---|---|---|
| AU | 2003238759 | 1/2004 |
| AU | 2004263067 | 2/2005 |
| AU | 2004305403 | 7/2005 |
| AU | 2011210083 | 8/2011 |
| AU | 2016266101 | 12/2016 |
| AU | 2017100469 | 5/2017 |
| AU | 2018220079 | 9/2018 |
| BR | 8701673 | 3/2009 |
| BR | 112012018909 | 1/2011 |
| CA | 2267812 | 10/2000 |
| CA | 2493331 | 1/2005 |
| CA | 2217476 C | 2/2006 |
| CA | 2561807 A1 | 12/2007 |
| CA | 2788153 | 8/2011 |
| CA | 2880138 | 2/2013 |
| CA | 2858905 | 10/2013 |
| CA | 2875637 | 1/2014 |
| CA | 2875578 | 12/2014 |
| CA | 2915843 | 12/2014 |
| CA | 2990620 | 12/2016 |
| CA | 2916286 | 6/2017 |
| CA | 3007296 | 6/2017 |
| CN | 1989895 | 7/2007 |
| CN | 201171316 | 12/2008 |
| CN | 101578516 | 11/2009 |
| CN | 101816290 | 9/2010 |
| CN | 101875975 | 11/2010 |
| CN | 101875976 | 11/2010 |
| CN | 102781225 | 1/2011 |
| CN | 102142116 | 8/2011 |
| CN | 102485892 | 6/2012 |
| CN | 102682322 | 9/2012 |
| CN | 203313865 | 12/2013 |
| CN | 203689049 | 2/2014 |
| CN | 203523519 | 4/2014 |
| CN | 204047531 | 8/2014 |
| CN | 104198002 A | 12/2014 |
| CN | 204305813 | 5/2015 |
| CN | 204331349 | 5/2015 |
| CN | 105191817 | 12/2015 |
| CN | 106125648 | 11/2016 |
| CN | 106172068 | 12/2016 |
| CN | 106197675 | 12/2016 |
| CN | 106719037 | 2/2017 |
| CN | 205919898 | 2/2017 |
| CN | 106472347 | 3/2017 |
| CN | 106845598 | 6/2017 |
| CN | 206431665 | 8/2017 |
| CN | 107201409 | 9/2017 |
| CN | 207201674 | 9/2017 |
| CN | 107251851 | 10/2017 |
| CN | 107667898 | 2/2018 |
| CN | 108353810 | 2/2018 |
| CN | 207100094 | 3/2018 |
| CN | 207249710 | 4/2018 |
| CN | 108651301 | 5/2018 |
| CN | 108656996 | 5/2018 |
| CN | 108684549 | 5/2018 |
| CN | 108118096 | 6/2018 |
| CN | 108308055 | 7/2018 |
| CN | 108401913 A | 8/2018 |
| CN | 109006541 | 8/2018 |
| CN | 109008529 | 8/2018 |
| CN | 108617533 | 10/2018 |
| CN | 108717668 | 10/2018 |
| CN | 108766586 | 11/2018 |
| CN | 109006550 | 12/2018 |
| CN | 208273869 | 12/2018 |
| CN | 109355402 | 2/2019 |
| CN | 109937904 | 3/2019 |
| CN | 109937905 | 3/2019 |
| CN | 109823691 | 5/2019 |
| CN | 110073995 | 5/2019 |
| CN | 110059781 | 7/2019 |
| CN | 110106261 | 8/2019 |
| CN | 110106262 | 8/2019 |
| CN | 110506656 | 11/2019 |
| CN | 210076292 | 2/2020 |
| DE | 633742 | 8/1936 |
| DE | 2850438 | 5/1980 |
| DE | 19629166 | 2/1997 |
| DE | 19826348 | 6/1998 |
| DE | 29906146 | 6/1999 |
| DE | 19911766 | 9/2000 |
| DE | 20018364 | 1/2001 |
| DE | 10001176 | 5/2001 |
| DE | 102004027978 | 12/2005 |
| DE | 202010008325 | 2/2012 |
| DE | 202013011075 | 1/2014 |
| DE | 202016101289 | 4/2016 |
| DK | 140001 | 11/1979 |
| EP | 55127 | 6/1982 |
| EP | 125915 | 11/1984 |
| EP | 0499428 | 8/1992 |
| EP | 513525 | 11/1992 |
| EP | 743043 | 11/1996 |
| EP | 938841 | 2/1998 |
| EP | 898449 | 3/1999 |
| EP | 1076485 | 2/2001 |
| EP | 1445723 | 8/2004 |
| EP | 1479338 | 11/2004 |
| EP | 1521208 | 4/2005 |
| EP | 1907816 | 4/2008 |
| EP | 1961294 | 8/2008 |
| EP | 2028931 | 3/2009 |
| EP | 2172878 | 4/2010 |
| EP | 2453733 | 5/2012 |
| EP | 2465344 | 6/2012 |
| EP | 2488237 | 8/2012 |
| EP | 2528431 | 12/2012 |
| EP | 2534945 | 12/2012 |
| EP | 2657889 | 10/2013 |
| EP | 2664234 | 11/2013 |
| EP | 2728995 | 5/2014 |
| EP | 2879615 | 6/2015 |
| EP | 2955998 | 12/2015 |
| EP | 3153098 | 4/2017 |
| EP | 3164855 | 5/2017 |
| EP | 3210531 | 8/2017 |
| EP | 3217566 | 9/2017 |
| EP | 3218865 | 9/2017 |
| EP | 3225106 | 10/2017 |
| EP | 3316680 | 5/2018 |
| EP | 3346422 | 7/2018 |
| EP | 3385886 | 10/2018 |
| EP | 3593634 | 1/2020 |
| EP | 3627856 | 3/2020 |
| EP | 3660855 | 6/2020 |
| ES | 2046912 | 2/1994 |
| ES | 2206009 | 5/2004 |
| ES | 2215152 | 10/2004 |
| ES | 1072416 | 7/2010 |
| ES | 2391341 | 11/2012 |
| ES | 1194609 | 10/2017 |
| FI | 20165318 | 6/2017 |
| FR | 2106705 | 5/1972 |
| FR | 2297565 | 8/1976 |
| FR | 2342024 | 1/1983 |
| FR | 2601848 | 1/1988 |
| FR | 2779153 | 12/1999 |
| FR | 2834521 | 7/2003 |
| FR | 2964777 | 3/2012 |
| FR | 3046332 | 1/2016 |
| FR | 3024653 | 2/2016 |
| FR | 3085249 | 9/2018 |
| GB | 588870 | 6/1947 |
| GB | 641394 | 8/1950 |
| GB | 865164 | 4/1961 |
| GB | 1072971 | 6/1967 |

(56) References Cited

FOREIGN PATENT DOCUMENTS

| | | |
|---|---|---|
| GB | 1267830 | 3/1972 |
| GB | 1415650 | 11/1975 |
| GB | 2067121 | 7/1981 |
| GB | 2055670 | 7/1983 |
| GB | 2114045 | 8/1983 |
| GB | 2125343 | 3/1984 |
| GB | 2142812 | 1/1985 |
| GB | 2152679 A * 8/1985 ................ A01J 5/01 |
| GB | 2392138 | 2/2004 |
| GB | 2469326 | 10/2010 |
| GB | 2554636 | 9/2016 |
| GB | 2570340 | 7/2019 |
| GB | 2571404 | 8/2019 |
| IN | 201103443 | 12/2011 |
| IN | 200802272 | 6/2016 |
| JP | 57173562 | 11/1982 |
| JP | 7177832 | 7/1995 |
| JP | 2001178692 | 7/2001 |
| JP | 2004292151 | 10/2004 |
| JP | 2005102959 | 4/2005 |
| JP | 5659243 | 1/2011 |
| JP | 2011067178 | 4/2011 |
| JP | 2011087657 | 5/2011 |
| JP | 2013247941 | 6/2012 |
| JP | 2017112857 | 6/2017 |
| JP | 2017002170 | 4/2018 |
| KR | 2003061157 | 7/2003 |
| KR | 2005046330 | 5/2005 |
| KR | 780449 | 11/2007 |
| KR | 101747418 | 1/2011 |
| KR | 20130019970 | 2/2013 |
| KR | 20130057683 | 6/2013 |
| KR | 2013138899 | 12/2013 |
| KR | 2019061805 | 11/2017 |
| KR | 101827311 | 2/2018 |
| KR | 201800355375 | 4/2018 |
| KR | 2018109451 | 10/2018 |
| KR | 20190081598 | 7/2019 |
| KR | 2019091708 | 8/2019 |
| MX | 9600754 | 2/1997 |
| MX | 356331 | 1/2011 |
| NL | 2017104 | 1/2018 |
| NL | 2019186 | 1/2019 |
| NL | 2020275 | 7/2019 |
| NZ | 198486 | 5/1986 |
| NZ | 199494 | 7/1986 |
| NZ | 203924 | 10/1986 |
| NZ | 335702 | 3/2001 |
| NZ | 507129 | 8/2002 |
| NZ | 582984 | 1/2011 |
| RU | 2178711 | 1/2002 |
| RU | 2265324 | 12/2005 |
| SE | 4567 | 3/1893 |
| SE | 5549 | 4/1894 |
| SE | 123213 | 11/1948 |
| SE | 188102 | 3/1964 |
| SU | 1766336 | 10/1992 |
| WO | 1984000468 | 2/1984 |
| WO | 1991011956 | 8/1991 |
| WO | 199302549 | 2/1993 |
| WO | 199822028 | 5/1998 |
| WO | 1998039475 | 9/1998 |
| WO | 1999017658 | 4/1999 |
| WO | 2000062263 | 4/1999 |
| WO | 9945761 | 9/1999 |
| WO | 2000013393 | 3/2000 |
| WO | 2000061802 | 10/2000 |
| WO | 2001033950 | 5/2001 |
| WO | 2001087054 | 11/2001 |
| WO | 2002031629 | 4/2002 |
| WO | 2002085106 | 10/2002 |
| WO | 2003001180 | 1/2003 |
| WO | 2004092920 | 3/2003 |
| WO | 2003087765 | 10/2003 |
| WO | 2003094605 | 11/2003 |
| WO | 2004015655 | 2/2004 |
| WO | 2005104775 | 4/2004 |
| WO | 2006078943 | 1/2005 |
| WO | 2005104930 | 4/2005 |
| WO | 2005073408 | 8/2005 |
| WO | 2006021855 | 3/2006 |
| WO | 2006134197 | 12/2006 |
| WO | 2006135265 | 12/2006 |
| WO | 2007034211 | 3/2007 |
| WO | 2007095684 | 8/2007 |
| WO | 2007122375 | 11/2007 |
| WO | 2008033042 | 3/2008 |
| WO | WO2008041839 A1 | 4/2008 |
| WO | 2008052298 | 5/2008 |
| WO | 2008075974 | 6/2008 |
| WO | 2010091686 | 12/2008 |
| WO | WO-2009020407 A2 * 2/2009 ............. A01J 5/041 |
| WO | 2009034497 | 3/2009 |
| WO | 2009062249 | 5/2009 |
| WO | 2009076325 | 6/2009 |
| WO | 2009089215 | 7/2009 |
| WO | 2009117764 | 10/2009 |
| WO | 2009153779 | 12/2009 |
| WO | 2010008620 | 1/2010 |
| WO | 2010048753 | 5/2010 |
| WO | 2010053811 | 5/2010 |
| WO | 2010068713 | 6/2010 |
| WO | 2010140900 | 12/2010 |
| WO | 2012075480 | 12/2010 |
| WO | 2011039112 | 4/2011 |
| WO | 2011076886 | 6/2011 |
| WO | 2011154949 | 12/2011 |
| WO | 2012071670 | 6/2012 |
| WO | 2013008115 | 1/2013 |
| WO | 2013038326 | 3/2013 |
| WO | 2013082227 | 6/2013 |
| WO | 2015001537 | 7/2013 |
| WO | 2013118121 | 8/2013 |
| WO | 2015024050 | 8/2013 |
| WO | 2013179020 | 12/2013 |
| WO | 2013190423 | 12/2013 |
| WO | 2014020463 | 2/2014 |
| WO | 2014095759 | 6/2014 |
| WO | 2014107766 | 7/2014 |
| WO | 2014118788 | 8/2014 |
| WO | 2014125250 | 8/2014 |
| WO | 2016027271 | 8/2014 |
| WO | 2014140148 | 9/2014 |
| WO | 2014141084 | 9/2014 |
| WO | 2014194383 | 12/2014 |
| WO | 2014197631 | 12/2014 |
| WO | 2014199363 | 12/2014 |
| WO | 2015009167 | 1/2015 |
| WO | 2015030832 | 3/2015 |
| WO | 2015055709 | 4/2015 |
| WO | 2015086338 | 6/2015 |
| WO | 2016207844 | 6/2015 |
| WO | 2015107354 | 7/2015 |
| WO | 2017001717 | 7/2015 |
| WO | 2017031532 | 8/2015 |
| WO | 2015140486 | 9/2015 |
| WO | 2015158787 | 10/2015 |
| WO | 2015175686 | 11/2015 |
| WO | 2015176027 | 11/2015 |
| WO | 2015197385 | 12/2015 |
| WO | 2016037190 | 3/2016 |
| WO | 2017149049 | 3/2016 |
| WO | 2016053104 | 4/2016 |
| WO | 2016108187 | 7/2016 |
| WO | 2016166748 | 10/2016 |
| WO | 2017001538 | 1/2017 |
| WO | 2017027551 | 2/2017 |
| WO | 2017037479 | 3/2017 |
| WO | 2017066813 | 4/2017 |
| WO | 2017089289 | 6/2017 |
| WO | 2017096256 | 6/2017 |
| WO | 2017121834 | 7/2017 |
| WO | 2018006965 | 1/2018 |
| WO | 2018011736 | 1/2018 |

(56) References Cited

FOREIGN PATENT DOCUMENTS

| WO | 2018019742 | | 2/2018 | |
|---|---|---|---|---|
| WO | 2018111093 | A1 | 6/2018 | |
| WO | 2020022543 | | 7/2018 | |
| WO | 2018172976 | | 9/2018 | |
| WO | 2020060248 | | 9/2018 | |
| WO | 2018203203 | | 11/2018 | |
| WO | 2019009717 | | 1/2019 | |
| WO | 2019025138 | | 2/2019 | |
| WO | 2019046216 | | 3/2019 | |
| WO | 2019058752 | | 3/2019 | |
| WO | WO2019048521 | A1 | 3/2019 | |
| WO | 2019071222 | | 4/2019 | |
| WO | 2019132803 | | 7/2019 | |
| WO | 2019207561 | | 10/2019 | |
| WO | 2019235942 | | 12/2019 | |
| WO | 2019245978 | | 12/2019 | |
| WO | 2020003310 | | 1/2020 | |
| WO | 2020096528 | | 5/2020 | |
| WO | 2020140013 | | 7/2020 | |
| WO | 2022189225 | A1 | 9/2022 | |
| WO | WO-2023222389 | A1 * | 11/2023 | ............... A01J 5/01 |

OTHER PUBLICATIONS

Steensels, Machteld; Maltz, Ephraim; Bahr, Claudia; Berckmans, Daniel; Antler, Aharon; et al., Towards practical application of sensors for monitoring animal health: The effect of post-calving health problems on rumination duration, activity and milk yield, The Journal of Dairy Research; Cambridge vol. 84, Iss. 2, (May 2017): 132-138.

Clark, C., Lyons, N., Millapan, L., Talukder, S., Cronin, G., Kerrisk, K., & Garcia, S. (2015), Rumination and activity levels as predictors of calving for dairy cows, Animal, 9(4), 691-695.

K. Koyama, T. Koyama, M. Sugimoto, N. Kusakari, R. Miura, K. Yoshioka, M. Hirako, Prediction of calving time in Holstein dairy cows by monitoring the ventral tail base surface temperature, The Veterinary Journal, vol. 240, 2018, pp. 1-5, ISSN 1090-0233.

L. Calamari, N. Soriani, G. Panella, F. Petrera, A. Minuti, E. Trevisi, Rumination time around calving: An early signal to detect cows at greater risk of disease, Journal of Dairy Science, vol. 97, Issue 6, 2014, pp. 3635-3647, ISSN 0022-0302.

S. Benaissa, F.A.M. Tuyttens, D. Plets, J. Trogh, L. Martens, L. Vandaele, W. Joseph, B. Sonck, Calving and estrus detection in dairy cattle using a combination of indoor localization and accelerometer sensors, Computers and Electronics in Agriculture, vol. 168, 2020, 105153, ISSN 0168-1699.

N. Soriani, E. Trevisi, L. Calamari, Relationships between rumination time, metabolic conditions, and health status in dairy cows during the transition period, Journal of Animal Science, vol. 90, Issue 12, Dec. 2012, pp. 4544-4554.

The role of sensors, big data and machine learning in modern animal farming; Suresh Neethirajan; Accepted Jul. 3, 2020 Sensing and Bio-Sensing Research 29 (2020) 1003672214-1804/ © 2020 The Author. Published by Elsevier B.V.

A Review on Determination of Computer Aid Diagnosis and/or Risk Factors Using Data Mining Methods in Veterinary Field Pinar Cihan, Erhan Gökçe, Oya Kalipsiz; Tekirdağ Namk Kemal University, Çorlu Faculty of Engineering, Department of Computer Engineering, Tekirdağ, Turkey. 2019.

Big Data Analytics and Precision Animal Agriculture Symposium: Data to decisions. B. J. White, D. E. Amrine, and R. L. Larson Beef Cattle Institute, Kansas State University, Manhattan, KS; © The Author(s) 2018. Published by Oxford University Press on behalf of American Society of Animal Science.

Gasteiner, J.; Boswerger, B.; Guggenberger, T., Practical use of a novel ruminal sensor on dairy farms, Praktische Tierarzt 2012 vol. 93 No. 8 pp. 730 . . . 739 ref.45.

Drying up Cows and the Effect of Different Methods Upon Milk Production; Ralph Wayne, C. H. Eckles, and W. E. Peterson; Division of Dairy Husbandry, University of Minnesota, St. Paul; Research-Article| vol. 16, Issue 1, p. 69-78, Jan. 1, 1933.

* cited by examiner

MILK CHANNEL AND FEED INLET COUPLED THERETO, AND SYSTEM AND METHOD FOR CONSERVING WASH FLUID IN A WASHING PROCESS FOR CLEANING A MILKMETER SYSTEM

TECHNICAL FIELD

The invention relates to milkmeter systems, including milkmeters with milk channels and feed inlets coupled thereto, and systems and methods for conserving wash fluid in washing processes for cleaning milkmeter systems.

BACKGROUND

Milkmeters in a milkmeter system measure a quantity of milk that is extracted from non-human mammals (e.g., cows, sheep, goats, etc.) over the course of a milking session. Food safety and public health regulations require that a milkmeter system be cleaned on a regular basis, for example, to avoid an accumulation of milk soil and/or bacteria in the milkmeter system. In order to clean the milkmeter system, water or wash fluid must be heated and then streamed throughout the milkmeter system. An object of the present disclosure is to ensure that the milkmeter system is cleaned while conserving resources, such as water, wash fluid, electricity, and/or power.

References considered to be relevant as background to the presently disclosed subject matter are listed below. Acknowledgement of the references herein is not to be inferred as meaning that these are in any way relevant to the patentability of the presently disclosed subject matter.

U.S. Patent Application Publication No. 2021/0262869 ("Pinsky et al."), published on Aug. 26, 2021, discloses a monitoring milk meter, which is able to monitor the livestock being milked, as well as general procedures performed in the milking farm, such as a Cleaning in Place (CIP) procedure.

GENERAL DESCRIPTION

In accordance with a first aspect of the presently disclosed subject matter, there is provided a device comprising: a milk channel having a first part and a second part, wherein a first value of at least one optical property of the first part is different than a second value of the optical property of the second part.

In some cases, at least a section of the milk channel includes four sides, wherein a first side of the sides is substantially opposite a second side of the sides, wherein both the first side and the second side are of a rectangular cross-section, and wherein the second part of the milk channel comprises a first window, being at least a portion of the first side of the sides, and a second window, being at least a second portion of the second side of the sides.

In some cases, the milk channel is a straight milk channel.

In accordance with a second aspect of the presently disclosed subject matter, there is provided a feed inlet, configured to be coupled to a milk conducting hose and to a milk channel of a milkmeter, the feed inlet comprising: a curved pipe having a first end and a second end, the first end having a first opening, enabling a fluid that flows through a milk conducting hose to enter the curved pipe, and the second end having a second opening for enabling the fluid to exit the curved pipe and enter the milk channel, wherein an angle of curvature between the first end and the second end is less than about 90 degrees.

In some cases, the feed inlet is configured to be coupled to the milk conducting hose via a hollow adaptor that extends between the milk conducting hose and the feed inlet.

In some cases, the feed inlet is configured to be coupled to the milk channel by connecting the second end of the curved pipe to an upper end of the milk channel.

In some cases, the angle of curvature is selected to increase an amount of time in which the milk channel is filled with the fluid.

In some cases, the angle of curvature is about 60 degrees.

In accordance with a third aspect of the presently disclosed subject matter, there is provided a wash fluid conservation system comprising a processing circuitry configured to: for one or more given milkmeters of one or more milkmeters in a milkmeter system, obtain, for one or more sampling periods during a given iteration of a given washing process for cleaning the milkmeter system, temperature values that are indicative of a temperature of a wash fluid that is flowing through the respective given milkmeter; and in response to the temperature values for a respective sampling period of the sampling periods being greater than or equal to a predefined temperature prior to a designated time for completion of the given iteration, perform one or more actions to reduce an amount of the wash fluid that is used in at least one of the given iteration or a subsequent iteration of the given washing process, subsequent to the given iteration, to be less than a designated amount of the wash fluid designated to be used in the given washing process in advance of the given iteration.

In some cases, the temperature values are obtained from one or more temperature sensors that are included in the given milkmeters.

In some cases, the actions include stopping the given iteration before the designated time.

In some cases, the given iteration is immediately stopped upon the temperature values for the respective sampling period being greater than or equal to the predefined temperature.

In some cases, the actions include designating a reduced amount of the wash fluid to be used in the subsequent iteration in advance of the subsequent iteration, the reduced amount being less than the designated amount.

In some cases, the processing circuitry is further configured to: calculate or determine an accumulated amount of the wash fluid that has flowed through the milkmeter system either: (a) during the given iteration or (b) until the end of the respective sampling period; wherein the reduced amount is designated to be greater than or equal to the accumulated amount.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings. The dimensions of components and features shown in the drawings are chosen for convenience and clarity of presentation and are not necessarily to scale. In the drawings.

DETAILED DESCRIPTION

Figure 1:
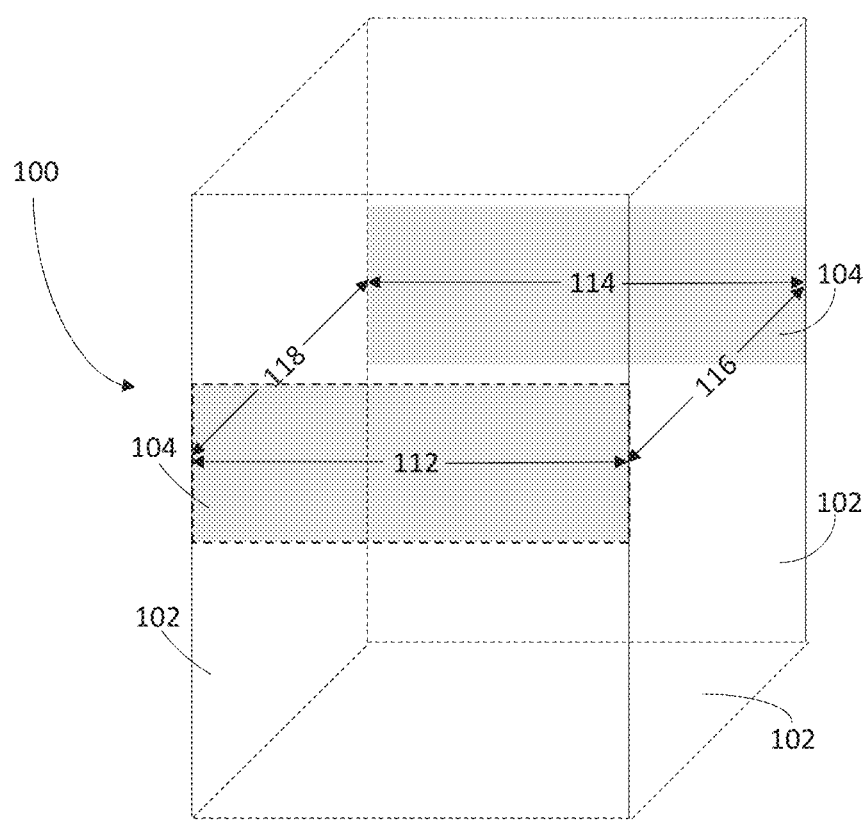
FIG. 1 is a schematic illustration of one example of a milk channel, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "calculating", "obtaining", "performing", "stopping", "designating" or the like, include actions and/or processes, including, inter alia, actions and/or processes of a computer, that manipulate and/or transform data into other data, said data represented as physical quantities, e.g. such as electronic quantities, and/or said data representing the physical objects. The terms "computer", "processor" and "processing circuitry" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field-programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 2:
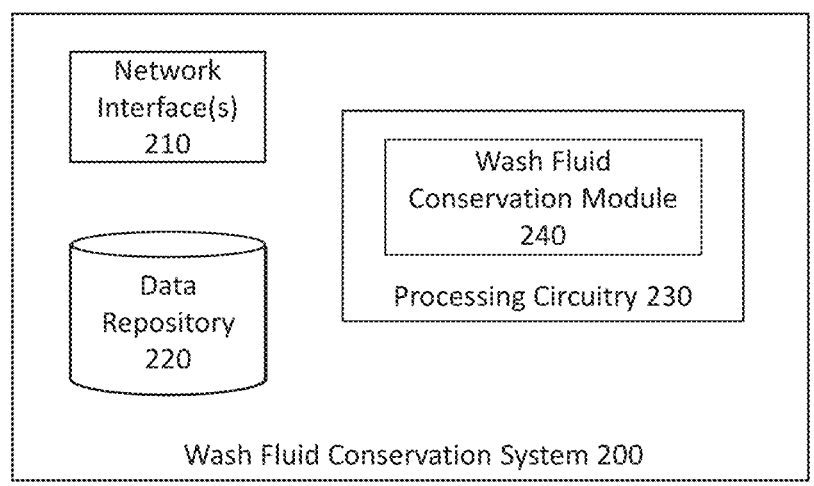
FIG. 2 is a block diagram schematically illustrating one example of a wash fluid conservation system, in accordance with the presently disclosed subject matter.
Figure 3:
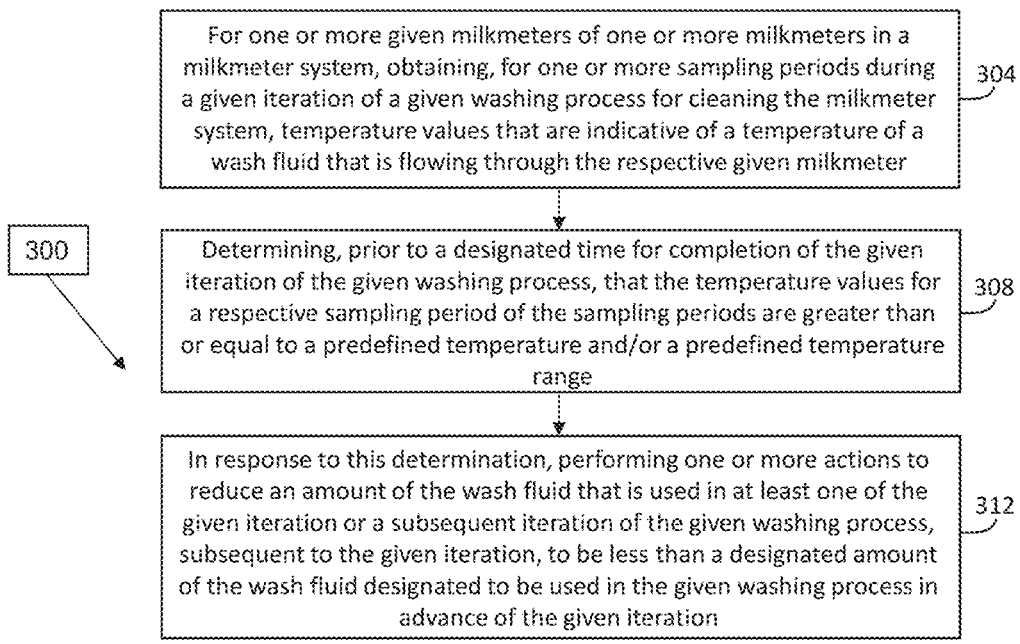
FIG. 3 is a flowchart illustrating one example of a sequence of operations for reducing an amount of a wash fluid that is used in at least one iteration of a given washing process for cleaning a milkmeter system comprising one or more milkmeters, in accordance with the presently disclosed subject matter.

In embodiments of the presently disclosed subject matter, fewer, more and/or different stages than those shown in FIG. 3. In embodiments of the presently disclosed subject matter, one or more stages illustrated in FIG. 3 may be executed in a different order and/or one or more groups of stages may be executed simultaneously. FIG. 2 illustrates a general schematic of a system architecture, in accordance with an embodiment of the presently disclosed subject matter. Each module in FIG. 2 can be made up of any combination of software, hardware and/or firmware that performs the functions as defined and explained herein. The modules in FIG. 2 may be centralized in one location or dispersed over more than one location. In other embodiments of the presently disclosed subject matter, the system may comprise fewer, more, and/or different modules than those shown in FIG. 2.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Attention is now drawn to FIG. 1, a schematic illustration of one example of a milk channel 100, in accordance with the presently disclosed subject matter.

In accordance with the presently disclosed subject matter, milk channel 100 is configured to enable a fluid (i.e, milk, a wash fluid, etc.) to flow therethrough. Milk channel 100 includes a first part 102 and a second part 104 (the second part 104 being shaded in grey in FIG. 1) wherein a first value of at least one optical property of the first part 102 is different than a second value of the optical property of the second part 104. In some cases, the milk channel 100 is a straight milk channel, as illustrated in FIG. 1. That is, the milk channel 100 is configured to enable a fluid (i.e., milk, a wash fluid, etc.) to flow through the milk channel 100 from a top of the milk channel 100 to a bottom of the milk channel 100 that is opposite, or substantially opposite, the top of the milk channel 100.

In some cases, at least a section of the milk channel 100 includes four sides 112, 114, 116 and 118; the second part 104 of the milk channel 100, shaded in grey; and at least some of the first part 102 of the milk channel 100. In some cases, all of the milk channel 100 to the exclusion of the second part 104 is the first part 102. In some cases, a first side 112 of the sides (112, 114, 116, 118) is substantially opposite a second side 114 of the sides (112, 114, 116, 118), and a third side 116 of the sides (112, 114, 116, 118) is substantially opposite a fourth side 118 of the sides (112, 114, 116, 118). In some cases, the first side 112 and the second side 114 are of a rectangular cross-section. In some cases, as illustrated in FIG. 1, the section of the milk channel 100 has a cubical structure. In some cases, the section of the milk channel 100 can have a structure other than a cubical structure, e.g., a tubular structure.

In some cases, the second part 104 of the milk channel 100 comprises a first window (shaded in grey in FIG. 1) being at least a portion of the first side 112 of the sides (112, 114, 116, 118), and a second window (shaded in grey in FIG. 1) being at least a portion of the second side 114 of the sides (112, 114, 116, 118). In some cases, the second part 104 of the milk channel 100 consists of the first window and the second window.

Attention is now drawn to FIG. 2, a block diagram schematically illustrating one example of a wash fluid conservation system 200, in accordance with the presently disclosed subject matter.

In accordance with the presently disclosed subject matter, wash fluid conservation system 200 can be configured to reduce an amount of wash fluid or water that is used in at least one iteration of a given washing process for cleaning a milkmeter system (not shown) comprising one or more milkmeters (not shown), the given washing process being at least part of a cleaning procedure for cleaning the milkmeter system. It is to be noted that all references in the present disclosure to the use of a wash fluid in a given washing process apply equally to the use of water in the given washing process. Moreover, it is to be noted that all references to a milkmeter in the present disclosure also apply to a milk sensor (i.e., a low-end milkmeter).

In some cases, wash fluid conservation system 200 can be configured to include one or more network interfaces 210. The network interfaces 210 are configured to connect the wash fluid conservation system 200 to one or more communications networks, thereby enabling the wash fluid conservation system 200 to send and receive data via the communications networks. In some cases, the communications networks can include an organizational (e.g., local) communications network for communications between milkmeters in the milkmeter system and the wash fluid conservation system 200. Additionally, or alternatively, in some cases, the communications networks can be configured to include an external communications network, such as the Internet, to enable the wash fluid conservation system 200 to communicate with other computerized devices that are external to the milkmeter system.

Wash fluid conservation system 200 can further comprise or be otherwise associated with a data repository 220 (e.g. a database, a storage system, a memory including Read Only Memory—ROM, Random Access Memory—RAM, and/or any other type of memory, etc.) configured to store data, including, inter alia, data received via the communications networks. In some cases, data repository 220 can be further configured to enable retrieval and/or update and/or deletion of the stored data. It is to be noted that in some cases, data repository 220 can be distributed.

Wash fluid conservation system 200 further comprises a processing circuitry 230. Processing circuitry 230 can be one or more processing units (e.g. central processing units), microprocessors, microcontrollers (e.g. microcontroller units (MCUs)) or any other computing devices or modules, including multiple and/or parallel and/or distributed processing units, which are adapted to independently or cooperatively process data for controlling relevant resources of the wash fluid conservation system 200 and for enabling operations related to resources of the wash fluid conservation system 200.

Processing circuitry 230 can be configured to include a wash fluid conservation module 240 for reducing an amount of the wash fluid that is used in at least one iteration of a given washing process for cleaning the milkmeter system, as detailed further herein, inter alia with reference to FIG. 3.

Attention is now drawn to FIG. 3, a flowchart illustrating one example of a sequence of operations 300 for reducing an amount of a wash fluid that is used in at least one iteration of a given washing process for cleaning a milkmeter system (not shown) comprising one or more milkmeters (not shown), in accordance with the presently disclosed subject matter.

In accordance with the presently disclosed subject matter, wash fluid conservation system 200 can be configured, e.g. using wash fluid conservation module 240, to obtain, for one or more given milkmeters of the milkmeters in the milkmeter system, temperature values that are indicative of a temperature of a wash fluid that is flowing through the respective given milkmeter during a given iteration of a given washing process of one or more washing processes for cleaning the milkmeter system. The temperature values are obtained for one or more sampling periods during the given iteration (block 304). In some cases, the sampling periods can be sampling instances.

The temperature values can be obtained from one or more temperature sensors (not shown). In some cases, the temperature sensors can be included in the given milkmeters. In some cases, the temperature sensor associated with a respective milkmeter of the milkmeters in the milkmeter system can be used to provide temperature values during a milking session for milking a non-human mammal, the temperature values being indicative of a temperature of milk that flows through the respective milkmeter during the milking session.

In some cases, one or more of the temperature sensors can be thermopiles. In some cases, all of the temperature sensors can be thermopiles.

Wash fluid conservation system 200 can be further configured, e.g. using wash fluid conservation module 240, to determine, prior to a designated time for completion of the given iteration of the given washing process, that the temperature values for a respective sampling period of the sampling periods are greater than or equal to a predefined temperature, and/or a predefined temperature range (block 308).

In response to this determination, wash fluid conservation system 200 can be configured, e.g. using wash fluid conservation module 240, to perform one or more actions to reduce an amount of the wash fluid that is used in at least one of the given iteration or a subsequent iteration of the given washing process, subsequent to the given iteration. The amount of the wash fluid is reduced to be less than a designated amount of the wash fluid designated to be used in the given washing process in advance of the given iteration (block 312). In some cases, the amount of the wash fluid that is used in more than one subsequent iteration of the given washing process can be reduced.

In some cases, the one or more actions are performed only upon the temperature values for one or more earlier sampling periods of the sampling periods of the given iteration preceding the respective sampling period of the given iteration being greater than or equal to the predefined temperature and/or the predefined temperature range. Additionally, or alternatively, in some cases, the one or more actions are performed not only based on the temperature values for the respective sampling period of the given iteration being greater than or equal to the predefined temperature and/or the predefined temperature range but also on the values of readings of one or more additional sensors (e.g., conductivity sensors, optical sensors, flow sensors that indicate the rate of flow of the wash fluid) that are associated with respective milkmeters in the milkmeter system and that are obtained during the given iteration of the given washing process. In this regard, it is to be noted that the readings from one or more of these additional sensors can also be provided during a milking session. For example, a conductivity sensor associated with a respective milkmeter of the milkmeters in the milkmeter system can be used to provide conductivity level readings during a milking session, the conductivity level readings being indicative of a conductivity of milk that flows through the respective milkmeter during the milking session.

In some cases, the actions can include stopping the given iteration of the given washing process before the designated time for completion of the given iteration. In so doing, resources (e.g., wash fluid, electrical power (e.g., electricity for heating the wash fluid that is used in the given iteration), a time duration of the given iteration, etc.) can be conserved. In some cases, the given iteration can be immediately stopped upon the temperature values for the respective sampling period during the given iteration being greater than or equal to the predefined temperature and/or the predefined temperature range.

Additionally, or alternatively, in some cases, the actions can include designating a reduced amount of the wash fluid to be used in a subsequent iteration(s) of the given washing process in advance of the subsequent iteration(s), the reduced amount being less than the designated amount of the wash fluid designated to be used in the given washing process in advance of the given iteration of the given washing process. In so doing, resources (e.g., wash fluid, electrical power (electricity for heating the wash fluid that is used in the subsequent iteration(s)), a time duration of the subsequent iteration(s), etc.) can be conserved for the subsequent iteration(s).

In some cases, wash fluid conservation system 200 can be configured, e.g. using wash fluid conservation module 240, to calculate or determine an amount of the wash fluid that has flowed through the milkmeter system either: (a) during the given iteration of the given washing process or (b) until the end of the respective sampling period of the given iteration (the calculated or determined amount of the wash fluid is referred to herein as the "accumulated amount of the wash fluid"). In one example, the accumulated amount of wash fluid may be calculated using flow sensors in the milkmeter system that indicate the rate of flow of the wash fluid. The accumulated amount of the wash fluid can then be used to determine a reduced amount of wash fluid to be used in subsequent iteration(s) of the given washing process. In some cases, the reduced amount of the wash fluid to be used in the subsequent iteration(s) can be equal to the accumulated amount of the wash fluid. Alternatively, in some cases, the reduced amount of the wash fluid to be used in the subsequent iteration(s) can be: (a) greater than the accumulated amount of the wash fluid and (b) less than the amount of the wash fluid that (absent use of the information from the accumulated amount of wash fluid) would have been used in the subsequent iteration(s). Thus, through using the information contained in the accumulated amount of the wash fluid, as described herein, the system may, in one example, use less wash fluid than it otherwise would have.

In some cases, the accumulated amount of the wash fluid can be calculated or determined, at least in part, by calculating or determining a respective amount of the wash fluid that has flowed through each milkmeter of the milkmeters in the milkmeter system either: (a) during the given iteration of the given washing process or (b) until the end of the respective sampling period of the given iteration (e.g., using flow sensors that indicate the rate of flow of the wash fluid through the milkmeters).

It is to be noted that, with reference to FIG. 3, some of the blocks can be integrated into a consolidated block or can be broken down to a few blocks and/or other blocks may be added. It should be also noted that whilst the flow diagrams are described also with reference to the system elements that realizes them, this is by no means binding, and the blocks can be performed by elements other than those described herein.

Figure 4:
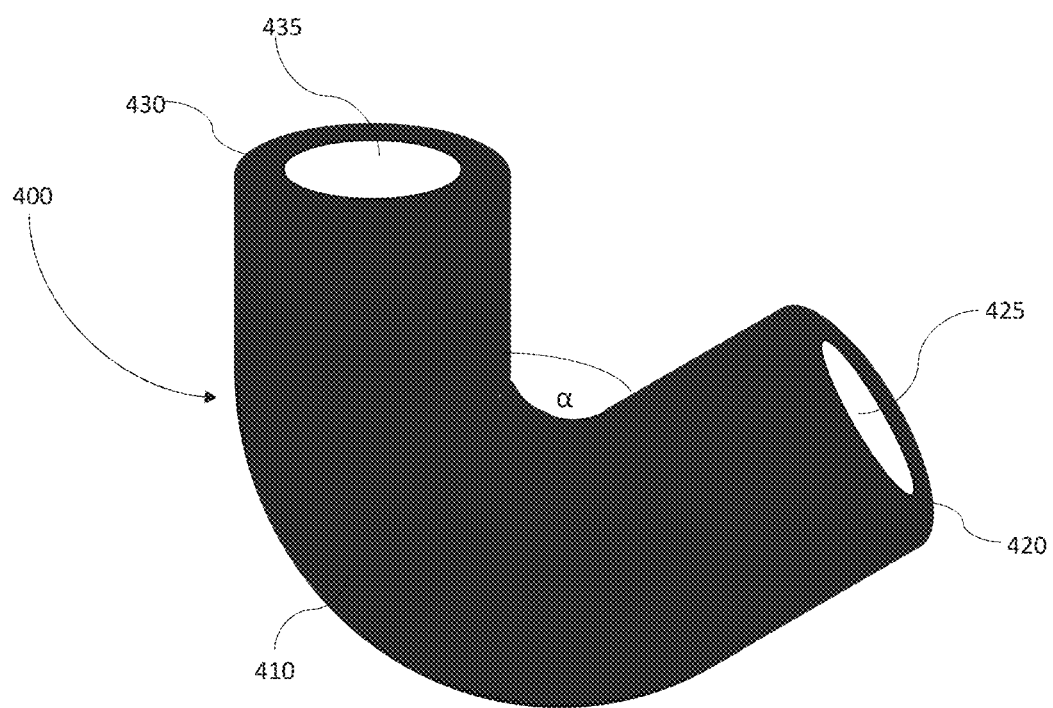
FIG. 4 is a schematic illustration of one example of a feed inlet configured to be coupled to a milk channel of a milkmeter, in accordance with the presently disclosed subject matter.

Attention is now drawn to FIG. 4, a schematic illustration of one example of a feed inlet 400 configured to be coupled to a milk channel 100 of a milkmeter, in accordance with the presently disclosed subject matter.

In accordance with the presently disclosed subject matter, feed inlet 400 can be configured to include a curved pipe 410 having a first end 420 and a second end 430. The first end 420 has a first opening 425, enabling a fluid that flows through a milk conducting hose (not shown in FIG. 4) to enter the curved pipe 410. In some cases, the fluid can be milk that is extracted from a non-human mammal during a milking session. In some cases, the fluid can be a wash fluid for cleaning the milking system, including, inter alia, the milk channel 100.

The second end 430 of the curved pipe 410 has a second opening 435. The second opening 435 enables the fluid that flows through the milk conducting hose and subsequently through the curved pipe 410 to exit the curved pipe 410 and enter the milk channel 100 of the milkmeter.

In some cases, the angle of curvature, a, between the first end 420 of the curved pipe 410 and the second end 430 of the curved pipe 410 can be less than about 90 degrees. In some cases, a can be between about 45 degrees to about 90 degrees. In some cases, a can be between about 50 degrees to about 75 degrees. In some cases, a can be between about 50 degrees to about 70 degrees (e.g., about 51, 52, 53, 54, 55, 56, 57, 58, 59, 60, 61, 62, 63, 64, 65, 66, 67, 68, 69, or 70 degrees).

Figure 5:
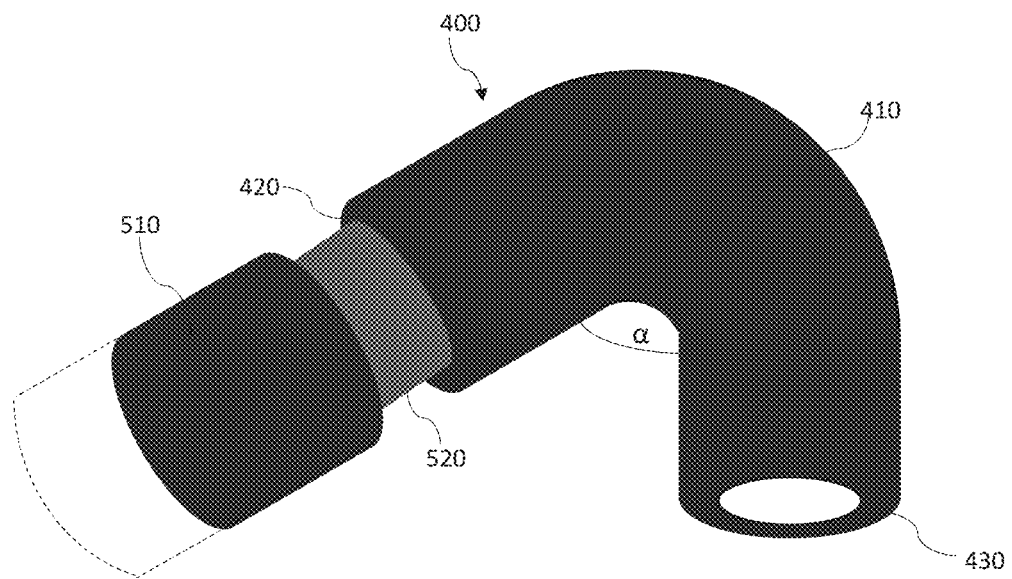
FIG. 5 is a schematic illustration of one example of a coupling of a feed inlet to a milk conducting hose and to a milk channel of a milkmeter, in accordance with the presently disclosed subject matter.

Attention is now drawn to FIG. 5, a schematic illustration of one example of a coupling of a feed inlet 400 to a milk conducting hose 510 and to a milk channel 100 of a milkmeter, in accordance with the presently disclosed subject matter.

In accordance with the presently disclosed subject matter, the feed inlet 400 is configured to be coupled to the milk conducting hose 510 and to the milk channel 100 (not shown in FIG. 5) to enable a fluid that flows through the milk conducting hose 510 to subsequently flow through the milk channel 100. In some cases, the feed inlet 400 can be coupled to a milk conducting hose 510 having a diameter of 16 mm. Alternatively, in some cases, the feed inlet 400 can be coupled, for example, to a milk conducting hose 510 having a diameter of 19 mm.

In some cases, as illustrated in FIG. 5, the feed inlet 400 can be configured to be coupled to the milk conducting hose 510 via a hollow adaptor 520 that extends between the milk conducting hose 510 and the feed inlet 400.

In some cases, the feed inlet 400 can be configured to be coupled to the milk channel 100 by connecting the second end 430 of the feed inlet 400 to an upper end of the milk channel 100 (not shown).

In some cases, the milk conducting hose 510 has a first cross sectional area and a section of the milk channel 100 (e.g., the section of the milk channel 100 illustrated in FIG. 1) has a second cross sectional area that is less than the first cross sectional area. It is advantageous to manufacture the section of the milk channel 100 to have a second cross sectional area that is less than the first cross sectional area of the milk conducting hose 510 since this allows for the milk channel 100 to be filled with a fluid (e.g., milk, a wash fluid, etc.) that is flowing through the milk channel 100 a greater percentage of the time during which the fluid is flowing through the milk channel 100, which can result in a more accurate calculation of an amount of the fluid that has passed through the milk channel 100. It is noted in this regard that the feed inlet 400 can be configured to connect to a milk channel 100 of a milkmeter, a milk sensor, or any other device in which there is a need or a benefit to having the milk channel 100 filled with a fluid (e.g., milk, a wash fluid, etc.).

In some cases, the angle of curvature, a, of the feed inlet 400 is selected to stream the fluid (e.g., milk, a wash fluid, etc.) to the milk channel 100 in bursts, i.e. the fluid is allowed to accumulate in the feed inlet 400 before it is streamed to the milk channel 100. By streaming the fluid to the milk channel 100 in bursts using the feed inlet 400 with the angle of curvature, a, the amount of time during the milking session and/or the cleaning procedure in which the milk channel 100 is filled with a fluid is increased. Moreover, by streaming the fluid to the milk channel 100 in bursts using the feed inlet 400 with the angle of curvature, a, the amount of the fluid that flows through the milk channel 100 during the milking session and/or the cleaning procedure can, at least in some cases, be more accurately calculated, at least in part due to the increase in the amount of time during the milking session and/or the cleaning procedure in which the milk channel 100 is filled with the fluid. In some cases, as detailed earlier herein, inter alia with reference to FIG. 4, a can be less than about 90 degrees. In some cases, a can be about 60 degrees.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

The invention claimed is:

1. A feed inlet, configured to be coupled to a milk conducting hose and to a milk channel of a milkmeter, the feed inlet comprising:
a curved pipe having a first end and a second end, the first end having a first opening, enabling a fluid that flows through a milk conducting hose to enter the curved pipe, and the second end having a second opening for enabling the fluid to exit the curved pipe and enter the milk channel, wherein an angle of curvature between the first end and the second end is less than about 90 degrees.

2. The feed inlet of claim 1, wherein the feed inlet is configured to be coupled to the milk conducting hose via a hollow adaptor that extends between the milk conducting hose and the feed inlet.

3. The feed inlet of claim 1, wherein the feed inlet is configured to be coupled to the milk channel by connecting the second end of the curved pipe to an upper end of the milk channel.

4. The feed inlet of claim 1, wherein the angle of curvature is selected to increase an amount of time in which the milk channel is filled with the fluid.

5. The feed inlet of claim 1, wherein the angle of curvature is about 60 degrees.

* * * * *

UNITED STATES PATENT AND TRADEMARK OFFICE
CERTIFICATE OF CORRECTION

| | | |
|---|---|---|
| PATENT NO. | : 12,402,596 B2 | Page 1 of 1 |
| APPLICATION NO. | : 17/735123 | |
| DATED | : September 2, 2025 | |
| INVENTOR(S) | : Cohen et al. | |

It is certified that error appears in the above-identified patent and that said Letters Patent is hereby corrected as shown below:

In the Claims

Claim 1 should read:
1. A feed inlet, configured to be coupled to a milk conducting hose and to a milk channel of a milkmeter, the feed inlet comprising:
a curved pipe having a first end and a second end, the first end having a first opening, enabling a fluid that flows through a milk conducting hose to enter the curved pipe, and the second end having a second opening for enabling the fluid to exit the curved pipe and enter the milk channel, wherein an angle of curvature between the first end and the second end is less than 90 degrees.

Signed and Sealed this
Twenty-third Day of December, 2025

John A. Squires
*Director of the United States Patent and Trademark Office*